United States Patent [19]

Keyes et al.

[11] 4,241,180
[45] Dec. 23, 1980

[54] ENZYMATIC METHOD FOR DETERMINING SURFACTANTS ON SURFACES

[75] Inventors: Melvin H. Keyes, Sylvania; Garry L. Moore, Swanton, both of Ohio

[73] Assignee: Owens-Illinois, Inc., Toledo, Ohio

[21] Appl. No.: 881,224

[22] Filed: Feb. 27, 1978

[51] Int. Cl.$^3$ ............................................. C12Q 1/46
[52] U.S. Cl. ......................................... 435/20; 435/4
[58] Field of Search ............. 195/103.5 R, 99; 435/4, 435/20, 174

[56] References Cited

U.S. PATENT DOCUMENTS

| | | | |
|---|---|---|---|
| 2,905,594 | 9/1959 | Morris | 195/103.5 R |
| 3,049,411 | 8/1962 | Gelman et al. | 195/103.5 R |
| 3,401,086 | 9/1968 | Hoffmann et al. | 195/103.5 R |
| 3,433,712 | 3/1969 | Gerarde | 195/103.5 R |
| 3,809,616 | 5/1974 | Schmitt et al. | 195/103.5 R |
| 3,837,806 | 9/1974 | Ritter et al. | 23/230 R |

OTHER PUBLICATIONS

Tsuji et al., *Chemical Abstracts*, 84:61671a, (1976).
Tsuji et al., *Chemical Abstracts*, 83:30300d, (1975).
Waters et al., *Analytica Chemica Acta*, 93, (1977), 341–344.
Tsuji et al., *J. of Amer. Oil Chem. Soc.*, 52(4), 111-114 (1975).

*Primary Examiner*—Esther M. Kepplinger
*Attorney, Agent, or Firm*—John R. Nelson; David H. Wilson; Myron E. Click

[57] ABSTRACT

A method for detecting the presence and quantitatively determining the amount of ionic or nonionic surfactants on a surface, particularly for the rapid determination of the surfactants on glass surfaces. The method comprises the use of an enzyme-substrate combination, including an enzyme which binds the ionic or nonionic surfactant on the surface, but is not deactivated, or inhibited, by the nonionic surfactant's binding. An indicator molecule is also present which is responsive to the product of the enzyme-substrate reaction. In operation, an aqueous solution of the enzyme and indicator is applied to the surface to be tested and sufficient time is allowed for any surfactant to dissolve and bind the enzyme. A solution of a standard ionic surfactant is then added which will bind and deactivate the enzyme if the enzyme has not been bound by any nonionic surfactant present. Finally, a solution of the enzyme substrate is added. Any color change in the test solution as a function of time, indicates the presence and concentration of the nonionic surfactant. To test for ionic surfactant, the step of addition of ionic surfactant may be omitted and the color change, if any, upon substrate addition is followed as a function of time.

13 Claims, No Drawings

ENZYMATIC METHOD FOR DETERMINING SURFACTANTS ON SURFACES

BACKGROUND OF THE INVENTION

1. Field of the Invention

The invention relates to methods for the determination of materials deposited on surfaces. Many areas of industry are in need of a reliable, rapid method to employ to detect surfactants. Many surfactants are used on metal surfaces for cleaning, and the complete removal of these cleaning surfactants must be checked prior to painting or further conditioning the surface. In the medical arts, hospitals check for the complete removal of cleaning surfactant on paperware, glassware and dishes which the patients use to insure purity of foods and drugs dispensed. Similarly, the cosmetic industry uses some surfactants in cosmetic preparations and the type and amount of these surfactants are needed to be followed for quality control. Particularly, the invention relates to a method for determining the presence on surfaces of surfactants, such as linear alkyl sulfonates, alkylarylsulfinates, linear long-chain carboxylic acids, such as oleic acid and its salts, and synthetic polymeric surfactants, such as polyoxyethylenestearates. The invention relates specifically to the detection and quantification of such surfactants on surfaces including non-ionic and ionic surfactants which have been deposited on the exterior surfaces of glass articles, particularly glass bottles and jars.

In the glass processing art, glass articles, bottles for example, are usually delivered to further processing stations after their formation to be packaged, polished, filled, or the like. As the glass articles are moved from one station to another, they frequently contact each other. This contact may result in abrasion on the surfaces of the glass which not only lessens the aesthetic value of the glass, but may also diminish the structural integrity of the glass.

To lessen the abrasion of the glass from these contacts, techniques have been developed to spray or otherwise coat a uniform layer of suitable surfactants onto the glass surfaces. When the coated glass articles contact each other, the tendency is for them to move against each other as frictionlessly as possible so as not to scratch or mar their surfaces.

Glass articles coated with surfactant are usually stored for long periods of time before their use. Uncoated articles may also be stored for long periods of time. When either coated or uncoated articles are returned for filling, labeling, etc., after having been stored for weeks or even months, it is difficult to know if a particular batch or lot of glassware has been treated or not treated with surfactant.

It is, therefore, desirable to have a method to detect if there is, in fact, a surfactant on the surface. Unfortunately, the surfactant coating is so thin that it is impossible to detect the presence by visual observation, and if present, in approximately what surface concentration. The method must be functional even in the areas of the production facilities like warehouses and loading docks, so that bottles and the like can be tested on-site and do not have to be removed to a laboratory for analysis. Additionally, the test should be simple, so that the average line worker may use the test without substantial training or expertise. Also, the test must be inexpensive and usable on a routine basis for on-line quality control in large-scale operations, as well as post-processing detection of surfactant.

DESCRIPTION OF THE PRIOR ART

Enzyme systems have been studied and used in the context of biological assay methods, for example, U.S. Pat. No. 2,905,594, issued to H. J. Morris, entitled "Means For Detecting Enzyme Activity." The Morris disclosure shows strips of test paper impregnated with reagents which show a vivid color on exposure to a moist tissue surface, typically a vegetable tissue such as potato dice, which contains an active enzyme.

The patent issued to C. G. Gelman and D. N. Kramer, U.S. Pat. No. 3,049,411, entitled "Enzymatic Method For Detection Of Anticholinesterase," discloses a test for various nerve gases which inhibit cholinesterase activity comprising forcing a volume of air suspected of containing the anticholinesterase agent through a moist filter pad which has adsorbed thereon a catalytically effective amount of cholinesterase. After exposure to this suspected nerve gas laden air, the pad is sprayed with a developer which shows color in a short time if active enzyme is still on the pad.

The patent to A. Hoffman et al., U.S. Pat. No. 3,410,086, entitled "Indicating Device And Method For The Determination Of Cholinesterase Activity In Serum," disclosed the method of determining serum cholinesterase concentrations by the use of a coupled reaction including an enzyme and an indicator dye. In the method, cholinesterase hydrolyzes its substrate acetylcholine to liberate acetic acid which produces a change in the color of a mixed indicator system, which comprises phenol red and alpha-naphtholphthalein.

This method and the others demonstrate the utilization of indirect substrate detection of the presence of an enzyme or inhibitor.

In recent years, enzyme technology has been increasingly used in non-biological detection and applications. One of the areas of possible use where enzyme methods may become important, is in the detection of surface materials for industry.

Two methods are generally in the art to determine a surface coating. The first method involves the scraping or dissolving of the surface material into a solvent, and performing a standard IR or UV analysis of the resultant solution. This method is somewhat cumbersome and time consuming.

An alternative method, is disclosed in the patent to J. R. Ritter and O. R. Strauch, U.S. Pat. No. 3,837,806, entitled "Method Of Analyzing Coatings On Particulate Material" showing a method for analyzing a glass which is coated with an aminosilane coupling agent which is assayed by reacting with silane with a saturated solution of 1-chloro-2, 4-dinitrobenzene, at elevated temperature, to produce a yellow color. The yellow color obtained is compared to a set of standard yellow colors representing a known thickness of the silane. This method, and similar chemical methods, usually require the instrumentation, equipment, and technical staff of an analytical laboratory. Thus, none of the tests presently known for the detection of surface coatings is simple, reliable in the field, and capable of being conducted easily by untrained personnel.

SUMMARY OF THE INVENTION

It is an object of the present invention to provide a method to simplify and reduce the cost of tests for surface materials.

Another object of the present invention is to provide a method for the detection of surfactants on surfaces which can be conducted in-the-field by non-technical personnel.

Another object of the present invention is to provide a method for the detection of surfactants which employs an enzyme reagent using a minimum of reagents and steps.

The present invention provides a method for the detection of surfactant on surfaces. Particularly, the method is used to detect nonionic surfactants which have been deposited on glass surfaces to reduce the abrasion thereof.

In an embodiment of the method of the invention in the testing of the presence and quantity of a nonionic surfactant on a surface, an enzyme-substrate combination is used including an enzyme which will bond nonionic surfactants, but will not be deactivated by the binding. An indicator is used therewith, which is responsive to the product of the enzyme-substrate reaction. An ionic surfactant is included which will bind the enzyme, and will by the binding, deactivate the enzyme. The enzyme, indicator, substrate, and ionic surfactant are each placed in suitably buffered solution.

To test for the nonionic surfactant, a quantity of the enzyme-indicator solution is applied to the surface and sufficient time is allowed for any nonionic surfactant present on the surface to dissolve into the enzyme-indicator solution. A quantity of ionic surfactant is added, followed by a quantity of the substrate of the enzyme. The change, and intensity of the change of the indicator color is monitored to give an indication of the presence and the quantity of the surfactant.

The test is rapid, on the order of a few minutes, and may be performed by non-technical employees with minimal training and difficulty. The reagents used are available in quantity, at reasonable prices. The low cost of the method makes its use practical in quality control procedures where large numbers of glass articles are tested.

DETAILED DESCRIPTION OF THE INVENTION

Some of the very difficult materials to test for in the art of surface material detection, are surfactants. Surfactants are compounds which, when dissolved in aqueous solution, lower the surface tension thereof. Surfactants are used in the cleaning industry, along with builders, to form the commonly found formulations called detergents. Other important uses of surfactants, both nonionic (such as polyoxyethylene tridecyl ether, and polyoxyethylene stearate) and ionic surfactants (such as potassium oleate) are as lubricants in surface coatings.

In glass manufacturing, when the glass articles come into contact with each other, there can be substantial marring or abrasion of the surface. This affects not only the aesthetic character of the article, but also, in some cases, the structural integrity of the article. To reduce this undesired abrasion, methods have been developed to spray or otherwise coat surfactants on glass surfaces to provide some lubricity to the surfaces, and thereby to lower the abrasion when contacting other glass articles.

Many commercial preparations have been used to coat glass and other surfaces for cleaning as well as antiabrasion purposes. For example, Renex 30 TM (a polyoxyethylene tridecyl ether), Renex 31 TM (a polyoxyethylene tridecyl ether), Myrj 52 S TM (a polyoxyethylene stearate), Myrj 53 TM (a polyoxyethylene stearate), Duracote TM (a polyethylene, potassium oleate composition) or Brij 35 TM (a polyethylene lauryl ether) have been widely used to produce a durable glassware lubricant which does no damage to the glass or to the contained product.

The coatings are, for all practical purposes, invisible, thin layers when placed on the bottles, jars, or any glass surface upon which they are coated. Therefore, when bottles have been stored in a warehouse for long periods of time, or being collected to be refilled, it is very difficult to visually detect the presence of the lubricant coating. This has presented a considerable problem in the glass industry and has encouraged the development of the present invention.

The present invention includes an enzymatic method for rapidly, inexpensively, and positively detecting the presence and quantity of such surfactants as set forth above. The method uses to advantage the special properties of enzymes, whereby an enzyme may bind a nonionic surfactant (NS) and maintain its catalytic activity towards its normal substrate. A substrate is a specific chemical compound with which an enzyme causes a chemical transformation. For example, the enzyme glucose oxidase will catalyze the reaction of glucose with oxygen to form gluconic acid and hydrogen peroxide. In this case, glucose is the substrate, glucose oxidase in the catalytically affective enzyme, and hydrogen peroxide and gluconic acid are the products. In regard to the present invention, an enzyme which binds an ionic surfactant will show a substantial, and in many cases, total loss of catalytic activity at a certain relatively low level of the ionic surfactant. These two properties of enzyme and surfactant chemistry form the theoretical basis of the present method.

The method, according to the present invention, employs an enzyme-substrate combination which includes an enzyme that will bind ionic surfactants (IS) and NS, and will be deactivated or inhibited by the IS, but will bind and not be deactivated by the NS. An indicator molecule (IND) is used which is responsive to the product of the enzyme substrate reaction, so that the production of the substrate breakdown products may be used to trigger a color change in the solution being observed.

Three solutions are used in the method of the invention. Solution ONE contains an appropriate buffer, and a few milligrams of the indicator e.g. phenol red (which shows red in color at about pH 8.2 and yellow in color at pH 6.8) and a predetermined amount of the enzyme. In the preferred embodiment of the present invention, the enzyme is purified cholinesterase. Solution TWO contains a predetermined concentration of an IS e.g. an alkyl aryl sulfonate. Solution THREE contains a predetermined amount of the enzyme substrate. In this case, the naturally occurring enzyme substrate of cholinesterase is acetylcholine (AC) used as the acetylcholine chloride. Solutions ONE and THREE are adjusted to a pH range of optimum activity of the particular enzyme. The enzyme cholinesterase, has a pH profile which shows a peak at about pH 7, so that the solutions are buffered to a slightly higher than 7 pH usually about 7.4 to 7.5.

According to the normal chemistry of cholinesterase (CE) if there is no surfactant of any kind present in the solution, the enzymatic reaction would proceed according to the equation shown in Reaction One.

Reaction One

AC + CE → acetic acid + choline + CE

If there is a NS present, it will bind the enzyme, according to the equation of Reaction Two, forming an enzymatically active complex.

Reaction Two

CE + NS + AC → CE·NS (active) + AC → acetic acid + choline + CE·NS (active)

If, however, there is an IS present, the enzyme binds it forming an inactive complex since the IS acts on an enzyme inhibiting reagent accordingly.

Reaction Three

CE + IS + AC → CE·IS (inactive) + AC → no reaction

To test for NS according to the method of the present invention, a small amount of Solution One, typically a few drops, are placed on the surface to be tested. If the surface has a marked curvature, an appropriate cap or retainer structure may be used to hold the liquid in place. A sufficient time is permitted so that any NS present on the surface can dissolve into the solution and bind the CE. Then a few drops of the IS, i.e. the inhibiting reagent, is added. Over the time period of the experiment, if there were NS on the surface, it has been bound by the CE and will not allow the binding of the enzyme deactivating inhibitor, in this case, the IS. Next, the solution of substrate, Solution Three, is added to initiate the reaction, here the normal enzyme-substrate reaction is shown in Reaction One. The CE·NS complex catalyzes the breakdown of the AC to form acetic acid and choline according to Reaction Two. The acetic acid then equilibrates to form acetate ion and hydrogen ion. The increasing concentration of the hydrogen ion lowers the solution pH and causes the IND to change from its "basic" color, red, to its "acidic" color yellow. Therefore, the overall reaction of interest shown in Reaction Four, is.

Reaction Four

CE·NS + IND (Red) + AC + IS → CE·NS + acetate ion + hydrogen ion IND (yellow) + IS + choline Thus the presence of the NS can be detected, according to the method of the present invention, by the color change of the solution. By adding standard amounts of reagents to Solutions One, Two, and Three, and placing controlled, standard amounts of the solutions on the surface, a quantitative measure of the NS surface concentration can be obtained. In order to quantify the NS, the time necessary to observe the color change and the intensity thereof can be related to standard color tables which allow for the quantitative determination of the NS surface concentration.

In practice, the three solutions are dispensed from dropper bottles with a standards chart so that a field employee simply adds a specified number of drops from bottle A, then a specific number of drops from bottle B, and then a specified number of drops from bottle C, and observes if there is a color change and the period of time for its appearance. The method when reduced to on-line practice is simple, relatively quick and when the reagents are used in quantity is inexpensive.

If the surface has been tested according to the above procedure, and found to have no NS, a second procedure allows for the testing of the surface for IS. To test for IS, Solution One is added and allows any IS present to bind the CE. This produces an inactive complex just as is the CE·IS complex shown in Reaction Three. The standard IS used in the present method is an alkyl aryl sulfonate, but other ionic surfactants will deactivate CE. Examples of other common ionic surfactants are potassium oleate; N-cetyl-N-ethyl morpholinium ethosulfonate; N-soya-Nethyl morpholinium ethosulfate and other common quaternary ammonium derivatives. After Solution One has been added, Solution Three is added. If there is no IS present, the CE catalyzes the generation of acetic acid and the corresponding IND color changes in a short time. If there is IS present, it will bind CE until all IS is bound to the CE. The remaining CE generates acetic acid and the corresponding time to color change gives an indication of the amount of the IS present. If there is sufficient IS to bind and deactivate all of the CE, no acetic acid is generated and no color change will occur. This will allow the determination of a particular IS up to an upper limit at which all enzyme is bound and deactivated.

Therefore, it is seen that the method according to the present invention allows for the rapid, simple determination of either NS or IS on a surface, particularly a glass surface. The following examples further illustrate the method according to the present invention.

EXAMPLE ONE

Preparation Of Solution One

A. Tris buffer i.e. tris(hydroxymethyl)aminomethane, is made by dissolving 0.243 g tris(hydroxymethyl)aminomethane in 50 ml of distilled water and adjusting to pH 7.4 with 0.1 M HCl, dilute to 100 ml with distilled water;

B. Magnesium chloride is made by dissolving 4.07 g of $MgCl_2.6H_2O$ in 100 ml distilled water, C. Prepare about 5 mg of phenol red in dry form;

D. Add to a 30 ml beaker 7 ml distilled water, 3 ml Tris, 3 ml magnesium chloride, the dry phenol red, shake 2-3 minutes until the solution is bright red in color.

E. Make a solution of 0.020 g of horse serum cholinesterase, butyryl type, purified (Worthington Biochemical Corp., Freehold, N.J.) in 20 ml distilled water.

F. Add 0.40 ml of E. to D.

Preparation of Solution Two

Solution Two is a 0.10 percent solution of a standard inhibitory species, here an alkyl aryl sulfonate, known commercially as G-3300 (Atlas Chemical Industries, Inc., Chemicals Division, Glass 800, surfactant G-3300). The solution is made by dissolving 0.1 ml Atlas G-3300 (lot 766) in 100 ml distilled water.

Preparation of Solution Three

Dissolve 8 g of acetylcholine chloride (Sigma Chemical Co.) in 10 ml distilled water, adjust the pH 7.4 with 0.1 M NaOH. Dilute the 10 ml as adjusted to 20 ml with distilled water.

Detection of NS

Step I

Using a pipette or dropper bottle, apply five to ten drops of Solution One to the surface of the bottle.

Step II

Apply three drops of the G-3300 solution, Solution Two.

Step III

Apply five drops Solution Three. Time the appearance of the yellow color. A typical set of time-concentration profiles are:

0.2 percent coating of polyoxyethylene stearate, time to yellow color about ten minutes;

5.0 percent coating of polyoxyethylene stearate, time to yellow color about three minutes.

Routine measurements are made when the surfactant concentration is on the order of 200 ppm in the test solution after dissolution of the surfactant off the surface and into the drops of test solutions added.

Detection of IS

Step I

Using a pipette or dropper bottle, apply five to ten drops of Solution one to the surface,

Step II

Apply five drops of Solution Three. Time the appearance of the yellow color and observe the intensity.

EXAMPLE TWO

Assay of Horse Serum Cholinesterase (CE)

Horse serum cholinesterase (CE) was assayed by the procedure described in the Worthington Enzyme Manual (Editor, Lillian A. Deckor, Worthington Biochemical Corp., Freehold, N.J. 1972, 1977) using a pH stat instrument, here the pH stat was the Sargent Welch, Model pHR pH stat which measures reaction rate by adding base to maintain a constant pH. The equivalents of base added per unit time is proportional to the reaction rate. This procedure involves preparing a 0.02 M TRIS-HCl buffer at pH 7.4 and 0.2 M $MgCl_2$ solution and a substrate solution of 2.2 M acetylcholine. These solutions are mixed in the following proportions:

- 3 ml of 0.2 M $MgCl_2$
- 3 ml of TRIS.HCl buffer
- 7 ml of distilled water
- 1 ml of enzyme solution (0.5 to 1 mg enzyme/ml $H_2O$)

The resulting solution is adjusted to pH 7.4 using the pH stat containing 0.02 M NaOH. After addition of 1 ml of 2.2 M acetylcholine, the pH stat maintains pH 7.5 by addition of aliquots of 0.02 M NaOH. Only the concentration of enzyme was varied to test this assay procedure. The test gives linear results from zero enzyme activity up to 6 U of enzyme activity.

EXAMPLE THREE

Immobilization of Cholinesterase on Filter Paper

Cholinesterase (CE) was immobilized for consistent application of enzyme in bottle testing. The procedure is as follows.

Twenty-five mg of CE (Worthington Biochemical Corp., Type: CPEP, Lot #55K439A) was dissolved in 10 ml of 1 mM TRIS HCl, pH 8.5. This mixture was stirred for one-half hour. To remove undissolved particles, the enzyme solution was filtered through a 0.2 $\mu$ TCM Gelman filter. Fifty filters of the same type (2.5 cm. diameter) were prepared for immobilization by washing with 1 M NaCl followed by 2 l of distilled water. The filters were mixed with the solution of CE and 30 ml of 0.11 M beta-mercapoethanol was added. This mixture was titrated to pH 6.0 with 0.01 M HCl and washed with 1 l of 0.1 M NaCl containing 1 mM TRIS HCl, pH 7.5. The final wash consisted of 500 ml of 1 mM TRIS HCl, pH 7.5 in which the filters were stored.

This CE-paper composite allows for the consistent application of a precise amount of the enzyme without the use of a dropping bottle where such use would be inconvenient. Example Four demonstrates the use of the filter paper method when the storage or use of soluble enzyme is not possible.

EXAMPLE FOUR

Filter Paper Support Material

Cholinesterase (CE) was absorbed onto filter paper obtained from Gelman Instruments, Inc. (TCM-200-25 mm diameter—0.2 micron pore size). The absorption solution contained 4.5 mM TRIS and 0.045 M $MgCl_2$ at pH 7.4. Total volume of the solution was 13.4 ml and a few milligrams of phenol red was added. A concentration of 0.02 mg/ml (see Example Two, above) of CE was used to prepare 10 filters.

To test bottle surfaces, the wet filter is placed on the bottles followed by one drop of a 0.1% G-3300 solution on top of filter. The reaction was started with the addition of one drop of a 2.2 M acetylcholine solution.

What is claimed is:

1. A method for determining the presence of either a non-ionic or ionic surfactant on a surface area without knowledge of whether the surfactant is either non-ionic or ionic, said method comprising:
   (a) applying to said area an enzyme adapted to bind with any surfactant present, said enzyme being bound without deactivation by a non-ionic surfactant and said enzyme being both bound and deactivated by an ionic surfactant, and an indicator responsive to a reaction product of said enzyme and a reactive substrate to exhibit a detectable response,
   (b) binding any surfactant present on said area by said enzyme,
   (c) adding an ionic surfactant to said area to bind and deactivate any unbound enzyme left by said first mentioned surfactant,
   (d) contacting said enzyme on said surface with a substrate reactive therewith, and
   (e) noting the presence or absence of a response by said indicator, the presence of a response indicating that said first mentioned surfactant was non-ionic, and the absence of a response indicating that said first mentioned surfactant was ionic.

2. The method according to claim 1, wherein the time from said contacting with said substrate to the noting of said response in said indicator is substantially proportional to the amount of surfactant on said surface area.

3. The method according to claim 1, wherein said surfactant to be determined is a nonionic surfactant.

4. The method according to claim 1, wherein said surfactant to be determined is an ionic surfactant.

5. The method according to claim 1, wherein said surface area is a glass surface.

6. The method according to claim 1, wherein said enzyme is a cholinesterase.

7. The method according to claim 1, wherein said substrate is a choline ester.

8. The method according to claim 7, wherein said choline ester is acetylcholine.

9. The method according to claim 1, wherein said indicator is phenol red.

10. The method according to claim 1, wherein said ionic surfactant is an anionic surfactant.

11. The method according to claim 10, wherein said anionic surfactant is an alkyl aryl sulfonate.

12. The method according to claim 1, wherein said selected enzyme is an immobilized enzyme.

13. The method according to claim 1, wherein said enzyme is an immobilized enzyme.

* * * * *